(12) United States Patent
Ghannoum et al.

(10) Patent No.: US 9,351,871 B2
(45) Date of Patent: May 31, 2016

(54) DISTAL PLASTIC END INFUSION/ASPIRATION TIP

(75) Inventors: Ziad R. Ghannoum, Trabuco Canyon, CA (US); Glenn Robert Sussman, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1220 days.

(21) Appl. No.: 12/269,373

(22) Filed: Nov. 12, 2008

(65) Prior Publication Data

US 2010/0121260 A1 May 13, 2010

(51) Int. Cl.
*A61F 9/007* (2006.01)
*A61M 1/00* (2006.01)

(52) U.S. Cl.
CPC .......... *A61F 9/00736* (2013.01); *A61M 1/0084* (2013.01); *A61M 2210/0612* (2013.01)

(58) Field of Classification Search
CPC ............. A61B 2017/320084; A61B 2217/005; A61B 17/3417; A61M 1/008; A61M 3/0279; A61M 1/0058; A61M 2210/0612
USPC ............... 604/27, 28, 35, 39, 43, 44, 45, 289, 604/290, 294, 521
See application file for complete search history.

(56) References Cited

U.S. PATENT DOCUMENTS

| | | | |
|---|---|---|---|
| 3,805,787 A | 4/1974 | Banko | |
| 4,014,333 A | 3/1977 | McIntyre | |
| 4,047,532 A | 9/1977 | Phillips et al. | |
| 4,204,328 A | 5/1980 | Kutner | |
| 4,386,927 A | 6/1983 | Eichenbaum | |
| 4,445,509 A | 5/1984 | Auth | |
| 4,487,600 A | 12/1984 | Brownlie et al. | |
| 4,519,385 A | 5/1985 | Atkinson et al. | |
| 4,531,943 A | 7/1985 | Van Tassel et al. | |
| 4,573,979 A | 3/1986 | Blake | |

(Continued)

FOREIGN PATENT DOCUMENTS

| CA | 2126860 AA | 6/1994 |
|---|---|---|
| DE | 197 00 809 | 7/1988 |

(Continued)

OTHER PUBLICATIONS

The ALCOM Silicone I/A Tip, Alcon 2007, Inc. CAT281.

(Continued)

*Primary Examiner* — Emily Schmidt
*Assistant Examiner* — Lauren M Peng
(74) *Attorney, Agent, or Firm* — Darien Reddick

(57) ABSTRACT

Embodiments described herein provide ophthalmic surgical instruments. One embodiment provides an instrument including an infusion sleeve, aspiration tube, and infusion/aspiration tip. The sleeve can include a body defining an infusion channel. The tube can be in the infusion channel and define an aspiration channel. The tip can conform to the distal end of the tube. The tip can seal a gap between the sleeve and tube and can include a flange with a profile (e.g., a tapered portion) corresponding to the profile of the sleeve. The sleeve and tip can be keyed such that the sleeve directs fluid in one direction and the tip draws fluid perpendicularly from that direction. The tip's aspiration channel can extend distally beyond its aspiration port. The tip can extend to a point adjacent to an infusion port of the sleeve. A disposable component (including an aspiration tube and infusion/aspiration tip) for use with instruments is provided.

26 Claims, 4 Drawing Sheets

(56) References Cited

U.S. PATENT DOCUMENTS

| | | | |
|---|---|---|---|
| 4,652,255 A * | 3/1987 | Martinez | A61F 9/00736 604/27 |
| 4,710,180 A | 12/1987 | Johnson | |
| 4,717,387 A | 1/1988 | Inoue et al. | |
| 4,813,926 A | 3/1989 | Kerwin | |
| 4,878,900 A | 11/1989 | Sundt | |
| 4,897,079 A | 1/1990 | Zaleski et al. | |
| 4,904,238 A | 2/1990 | Williams | |
| 4,921,482 A | 5/1990 | Hammerslag et al. | |
| 4,983,160 A | 1/1991 | Steppe et al. | |
| 4,998,916 A | 3/1991 | Hammerslag et al. | |
| 4,998,923 A | 3/1991 | Samson et al. | |
| 5,037,391 A | 8/1991 | Hammerslag et al. | |
| 5,084,009 A | 1/1992 | Mackool | |
| 5,084,012 A | 1/1992 | Kelman | |
| 5,106,381 A | 4/1992 | Chikama | |
| 5,108,368 A | 4/1992 | Hammerslag et al. | |
| 5,133,159 A | 7/1992 | Nelson | |
| 5,151,084 A | 9/1992 | Khek | |
| 5,176,126 A | 1/1993 | Ckikama | |
| 5,203,772 A | 4/1993 | Hammerslag et al. | |
| 5,217,465 A | 6/1993 | Steppe | |
| 5,242,449 A | 9/1993 | Zaleski | |
| 5,286,256 A | 2/1994 | Mackool | |
| 5,290,892 A | 3/1994 | Namdaran et al. | |
| 5,292,310 A | 3/1994 | Yoon | |
| 5,308,324 A | 5/1994 | Hammerslag et al. | |
| 5,328,456 A | 7/1994 | Horiguchi | |
| 5,354,265 A | 10/1994 | Mackool | |
| 5,358,507 A | 10/1994 | Daily | |
| 5,364,405 A | 11/1994 | Zaleski | |
| 5,372,587 A | 12/1994 | Hammerslag et al. | |
| 5,378,234 A | 1/1995 | Hammerslag et al. | |
| 5,381,782 A | 1/1995 | Delarama et al. | |
| 5,403,901 A | 4/1995 | Namdaran et al. | |
| 5,421,955 A | 6/1995 | Lau et al. | |
| 5,433,746 A | 7/1995 | Namdaran et al. | |
| 5,441,496 A | 8/1995 | Easley et al. | |
| 5,451,229 A | 9/1995 | Geuder et al. | |
| 5,514,086 A | 5/1996 | Parisi et al. | |
| 5,522,826 A | 6/1996 | Daily | |
| 5,603,710 A | 2/1997 | Easley et al. | |
| 5,645,530 A | 7/1997 | Boukhny et al. | |
| 5,693,062 A | 12/1997 | Stegmann et al. | |
| 5,718,677 A | 2/1998 | Capetan et al. | |
| 5,830,192 A | 11/1998 | Van Voorhis | |
| 5,836,926 A | 11/1998 | Peterson et al. | |
| 5,873,851 A | 2/1999 | Nilsson | |
| 5,921,998 A | 7/1999 | Tano et al. | |
| 5,957,928 A | 9/1999 | Kirwan, Jr. | |
| 5,989,209 A | 11/1999 | Barrett | |
| 6,007,513 A | 12/1999 | Anis et al. | |
| 6,007,555 A | 12/1999 | Devine | |
| 6,013,049 A | 1/2000 | Rockley et al. | |
| 6,068,641 A | 5/2000 | Varsseveld | |
| 6,117,151 A | 9/2000 | Urich et al. | |
| 6,132,426 A | 10/2000 | Kroll | |
| 6,299,591 B1 | 10/2001 | Banko | |
| 6,340,355 B1 | 1/2002 | Barrett | |
| 6,398,759 B1 | 6/2002 | Sussman et al. | |
| 6,428,501 B1 | 8/2002 | Reynard | |
| 6,491,670 B1 | 12/2002 | Toth et al. | |
| 6,520,929 B2 | 2/2003 | Zaleski | |
| 6,544,254 B1 | 4/2003 | Bath | |
| 6,579,270 B2 | 6/2003 | Sussman et al. | |
| 6,592,541 B1 | 7/2003 | Kurwa | |
| 6,623,477 B1 | 9/2003 | Elbrecht et al. | |
| 6,852,093 B1 | 2/2005 | Boukhny | |
| 6,902,558 B2 | 6/2005 | Laks | |
| 7,014,629 B2 | 3/2006 | Mackool | |
| 7,066,923 B2 | 6/2006 | Tjia | |
| 7,094,229 B2 | 8/2006 | Boukhny et al. | |
| 7,211,074 B2 * | 5/2007 | Sansoucy | 604/537 |
| 7,329,261 B2 | 2/2008 | Perkins | |
| 2003/0004455 A1 | 1/2003 | Kadziauskas et al. | |
| 2003/0069594 A1 | 4/2003 | Rockley et al. | |
| 2003/0199883 A1 | 10/2003 | Laks | |
| 2003/0208218 A1 | 11/2003 | Kadziauskas | |
| 2004/0068270 A1 | 4/2004 | Allred | |
| 2004/0089080 A1 | 5/2004 | Kadziauskas | |
| 2004/0092921 A1 | 5/2004 | Kadziauskas et al. | |
| 2004/0153093 A1 | 8/2004 | Donovan | |
| 2005/0171469 A1 | 8/2005 | Cunningham | |
| 2005/0234473 A1 | 10/2005 | Zacharias | |
| 2005/0256462 A1 | 11/2005 | Underwood | |
| 2005/0277898 A1 | 12/2005 | Dimalanta et al. | |
| 2005/0288650 A1 | 12/2005 | Boukhny et al. | |
| 2006/0036215 A1 | 2/2006 | Boukhny | |
| 2006/0047241 A1 | 3/2006 | Boukhny | |
| 2006/0212038 A1 | 9/2006 | Boukhny | |
| 2007/0244425 A1 | 10/2007 | Pond | |
| 2008/0167604 A1 | 7/2008 | Hong | |
| 2010/0121260 A1 | 5/2010 | Ghannoum et al. | |
| 2012/0143125 A1 | 6/2012 | Lane | |

FOREIGN PATENT DOCUMENTS

| | | |
|---|---|---|
| DE | 4313245C2 C2 | 3/1997 |
| EP | 0778 039 A1 | 6/1997 |
| EP | 1371347 A2 | 12/2003 |
| EP | 1607076 | 12/2005 |
| EP | 1607077 A1 | 12/2005 |
| EP | 1852095 A1 | 11/2007 |
| FR | 2713492 A1 | 6/1995 |
| JP | H04-5166 | 1/1992 |
| JP | H09-253215 | 9/1997 |
| JP | 10071166 A | 3/1998 |
| JP | 2007-521913 | 8/2007 |
| JP | 2008-518707 | 6/2008 |
| WO | 9807398 | 8/1997 |
| WO | WO 99/11313 | 3/1999 |
| WO | 0228449 A3 | 4/2002 |
| WO | 2007006466 | 1/2007 |
| WO | 2010056448 A1 | 5/2010 |
| WO | 2012078319 A1 | 6/2012 |

OTHER PUBLICATIONS

International Search Report for PCT/US2009/060315, Publication No. WO2010/056448, 4 pages.
The Alcon Silicone I/A Tip, Alcon Inc., Cataract Product Catalog, Sep. 2008, CAT281, 3 pages.
PCT International Preliminary Report on Patentability, PCT/US2009/060315, May 17, 2011, 7 pages.
Dr. Ulrich Naumann, Notice of Opposition and EPO Communication, Sep. 23, 2010, 44 pages. (3093).
International Searching Authority, Written Opinion of the International Searching Authority, PCT/US2009/060315, Jan. 12, 2010, 6 pages. (3476).
Prosecution History of European Patent No. 1852095, filed Apr. 25, 2007.
Dr. Ulrich Naumann, English translation of Opposition letter, Sep. 27, 2012, 7 pages.
English translation of Sep. 26, 2011 submission and English translation of Opponent letter dated Aug. 31, 2011, 7 pages.
International Searching Authority, International Search Report, PCT/US2011/030751, Feb. 6, 2012, 3 pages. (3804).
International Searching Authority, Written Opinion of the International Searching Authority, PCT/US2011/030751, Feb. 6, 2012, 4 pages. (3804).

* cited by examiner

DISTAL PLASTIC END INFUSION/ASPIRATION TIP

BACKGROUND OF THE INVENTION

Embodiments relate generally to the field of ophthalmic surgery and more particularly to instruments and methods for removing cataracts.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age, disease, trauma, etc. causes the lens to become less transparent, vision deteriorates because of the diminished light which can be transmitted to the retina. This deficiency in the lens of the eye is medically known as a cataract. A generally accepted treatment for this condition is surgical removal and replacement of the lens with an artificial intraocular lens (IOL).

SUMMARY OF THE INVENTION

Embodiments described herein provide instruments for infusion and aspiration during eye surgery.

One embodiment provides an instrument including an infusion sleeve, an aspiration tube, and an infusion/aspiration tip. The infusion sleeve can include a body which defines an infusion channel. The aspiration tube can be positioned in the infusion channel and can define an aspiration channel. The infusion/aspiration tip can couple to and conform to the distal end of the aspiration tube. The infusion/aspiration tip can seal a gap between the infusion sleeve and the aspiration tube. Furthermore, in some embodiments, the infusion/aspiration tip can include a flange with a profile (e.g., a tapered portion) corresponding to a profile of the infusion sleeve. In some embodiments, the infusion sleeve and the infusion/aspiration tip can be keyed such that the infusion sleeve directs fluid in one direction and the infusion/aspiration tip aspirates material from another direction. The infusion and aspiration directions can be perpendicular to each other. The aspiration channel of the infusion/aspiration tip can extend distally beyond the aspiration port. In some embodiments, the infusion/aspiration tip can extend proximally to a point adjacent to an infusion port of the sleeve.

One embodiment provides a single use, disposable component for use with an ophthalmic surgical instrument. The instrument can include an infusion sleeve comprising an elongated body defining an infusion channel and having a proximal end, a distal end, and a longitudinal axis along the length of the elongated body whereas the component can include an aspiration tube and an infusion/aspiration tip. The aspiration tube can define an aspiration channel and can have a proximal end and a distal end. When the disposable component is in the instrument, the aspiration tube can be positioned in the infusion channel. The infusion/aspiration tip can couple to and conform to the distal end of the aspiration tube.

In some embodiments, when the disposable component is coupled to the instrument, a gap can exist between the distal end of the infusion sleeve and the distal end of the aspiration tube. The infusion/aspiration tip can seal the gap when the disposable component is coupled to the instrument. The infusion/aspiration tip can define an aspiration port oriented to draw material from the environment from a direction which is perpendicular to the longitudinal axis of the disposable component and perpendicular to the direction in which an infusion port of the infusion sleeve directs infusion fluid when the disposable component is coupled to the instrument. In some embodiments, when the disposable component is coupled to the instrument, the infusion/aspiration tip can extend in a direction along the longitudinal axis to a point adjacent to the infusion port.

Embodiments provide instruments which reduce patient trauma during cataract extraction and other ophthalmic procedures. More particularly, embodiments provide instruments which reduce, if not eliminate, the possibility of tears in capsular bags due to micro burrs on various instruments. Embodiments provide inexpensive and disposable aspiration tubes for ophthalmic instruments. In some embodiments, leakage of infusion fluid between the infusion sleeve and the infusion/aspiration tip can be eliminated or greatly reduced. Embodiments eliminate the need to clean aspiration tubes and infusion/aspiration tips of various ophthalmic surgical instruments following surgery.

BRIEF DESCRIPTION OF THE FIGURES

A more complete understanding of the present invention and the advantages thereof may be acquired by referring to the following description, taken in conjunction with the accompanying drawings in which like reference numbers indicate like features.

DETAILED DESCRIPTION

Preferred embodiments are illustrated in the FIGURES, like numerals generally being used to refer to like and corresponding parts of the various drawings.

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example", "for instance", "e.g.", "in one embodiment".

Previously, to remove a lens from an eye, surgical personnel sometimes used an ophthalmic instrument with an infusion sleeve and an aspiration tube therein. Surgical personnel also used a sleeve made of silicon and having a hole therein for aspirating fluid. Surgical personnel slipped the sleeve over the aspiration tube and then used the instrument for ophthalmic surgery. The sleeves, though, were often difficult to use. For instance, the sleeves could tear thereby making it necessary to remove and replace the damaged sleeve. In addition, once on the aspiration tube, these sleeves could slip off of the aspiration tube making its replacement on the aspiration tube necessary. Moreover, because these sleeves only partially filled the space between the aspiration tube and the infusion tube, some infusion fluid could leak out of the distal end of the instrument and move in a forward direction and into the eye. This condition can be undesirable because surgical personnel typically prefer that the instrument direct the infusion fluid perpendicularly from the instrument while aspirating material longitudinally from the distal end of the instrument.

Figure 1:
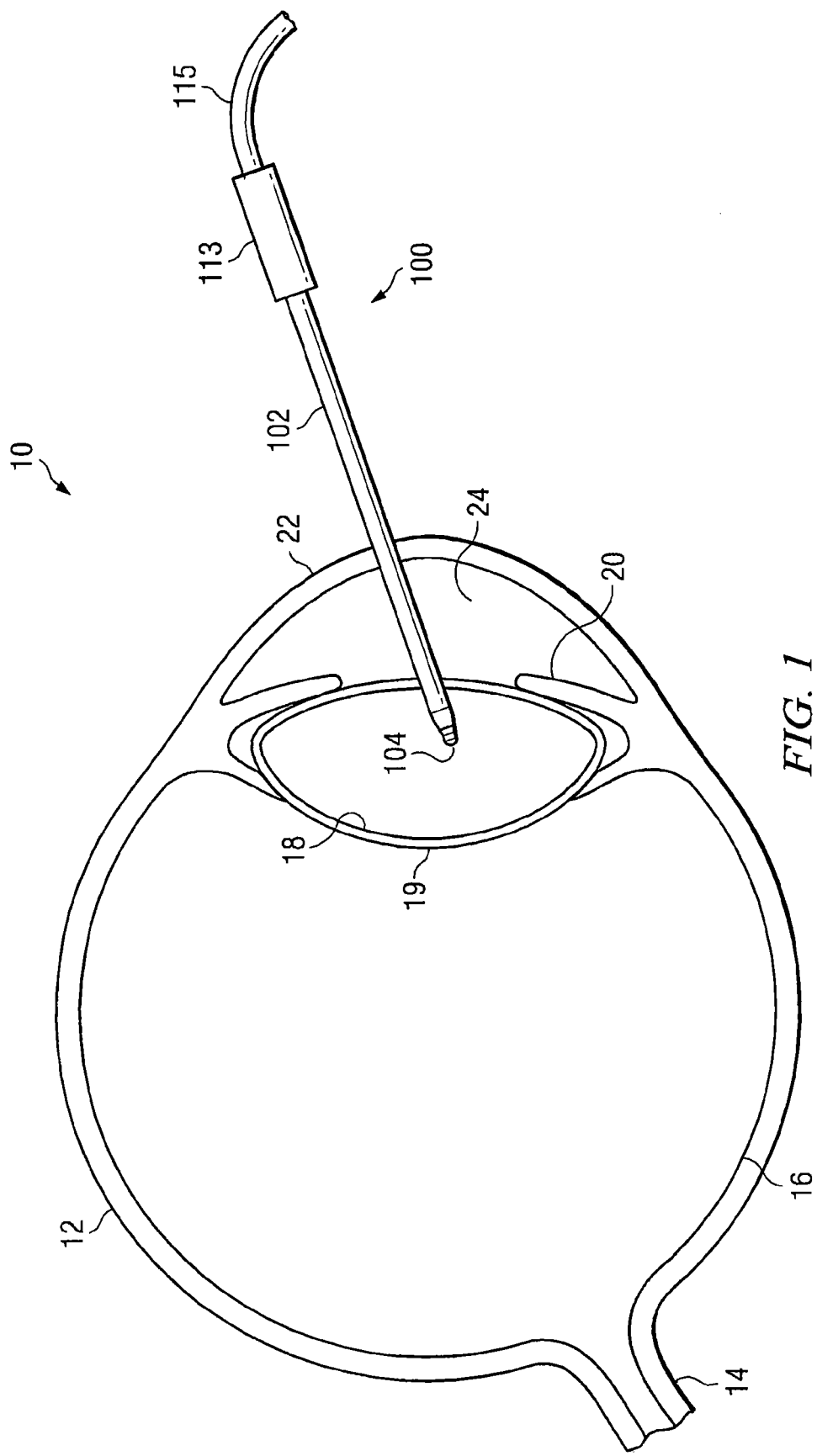
FIG. 1 is a cross sectional view of an eye undergoing ophthalmic surgery.

With reference now to FIG. 1, a cross sectional view of eye 10 undergoing ophthalmic surgery is illustrated. The procedure illustrated could be a cataract extraction. Eye 10 includes sclera 12, optic nerve 14, retina 16, lens 18, capsular bag 19, iris 20, cornea 22, and pupil 24. Normally, lens 18 focuses light passing through cornea 22 and pupil 24 on to retina 16. Retina 16 converts light to nerve impulses which retina 16 sends along optic nerve 14 to the brain. Iris 20 regulates the amount of light passing through pupil 24 and lens 18 thereby allowing eye 10 to adapt to varying levels of light. Capsular bag 19 holds lens 18 in place and is transparent so that light may pass through it. Thus, the nerve impulses traveling along optic nerve 14 correspond to scenes visible to eye 10.

However, various diseases, conditions, injuries, etc. can cause lens 18 to become clouded, translucent, etc. to the point that it might be desirable to extract lens 18 from eye 10. In such situations, the affected patient can be said to have a "cataract." Often, when lens 18 is removed from eye 10 (i.e., the cataract is extracted), surgical personnel replace lens 18 with an artificial lens, thereby restoring sight to the affected patient. Alcon Laboratories, Inc. (of Fort Worth, Tex.) provides exemplary artificial lenses such as the AcrySof® intraocular lenses. To remove lens 18, surgical personnel sometimes use instrument 100. As illustrated by FIG. 1, instrument 100 can include elongated infusion sleeve 102, infusion/aspiration tip 104, and handpiece 113. Ophthalmic tubing 115 can be connected to instrument 100 at handpiece 113 and can supply infusion fluid from an infusion/aspiration machine to instrument 100 and return material aspirated from eye 10 to the infusion/aspiration machine. Handpiece 113 can provide communication channels between ophthalmic tubing 115 and infusion sleeve 102 and infusion/aspiration tip 104. Additionally, handpiece 113 can couple with infusion sleeve 102 and indirectly with infusion/aspiration tip 104 (via one or more internal components) thereby holding these components 102 and 104 in fixed operational relationship to each other.

To extract the cataract, surgical personnel can make an incision in cornea 22 and capsular bag 19. Through the incision, surgical personnel can insert infusion/aspiration tip 104 of instrument 100 into lens 18. Using instrument 100, surgical personnel can direct infusion fluid from infusion/aspiration tip 104 into lens 18 thereby causing lens 18 to disintegrate. Infusion/aspiration tip 104 can draw the infusion fluid, cortical material, and portions of disintegrated lens 18 from capsular bag 19. At some time, surgical personnel can withdraw instrument 100 from eye 10, insert an artificial lens into capsular bag 19 of eye 10, and close the incision.

Previously, during such procedures, micro burrs on surfaces of previously available instruments would catch on, and tear, capsular bag 19. Furthermore, forward leakage of infusion fluid from previously available instruments could interfere with aspiration of material from capsular bag 19. Forward leakage can reduce the efficiency of various surgical techniques and increase the time necessary for performing such techniques. Embodiments of instrument 100, though, can have a smooth, relatively micro burr-free, surfaces. Thus, embodiments of instrument 100 can reduce, if not eliminate, capsular bag 19 tears caused by micro burrs while increasing the speed and efficiency of various ophthalmic techniques.

Figure 2:
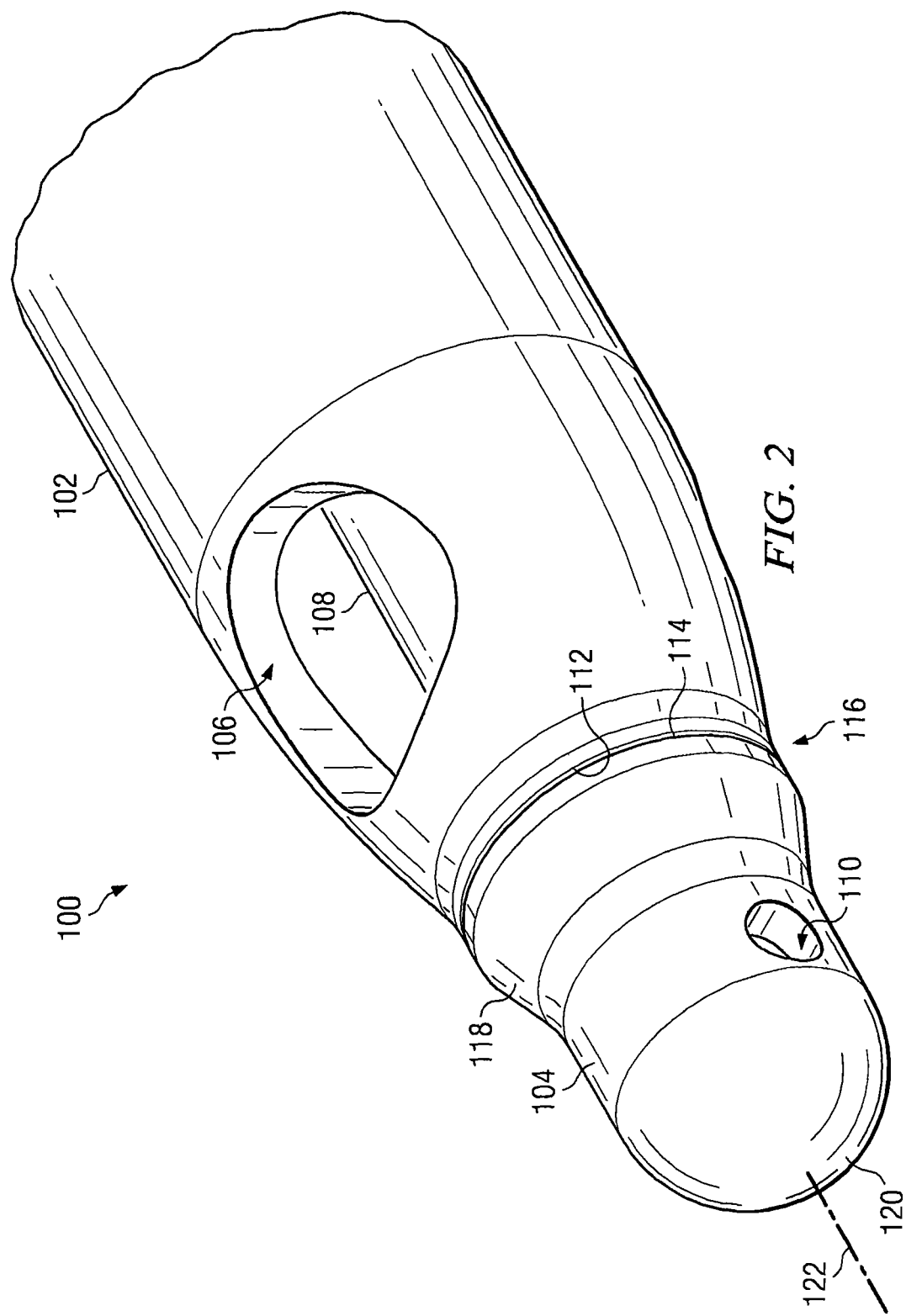
FIG. 2 is a perspective view of one embodiment of an ophthalmic surgical instrument.

FIG. 2 further illustrates instrument 100 including infusion sleeve 102, infusion/aspiration tip 104, infusion port 106, aspiration tube 108, aspiration port 110, distal end 112 of infusion sleeve 102, flange 114 of infusion/aspiration tip 104, proximal end 116 of infusion/aspiration tip 104, tapered portion 118 of infusion/aspiration tip 104, distal end 120 of infusion/aspiration tip 104, and longitudinal axis 122 of instrument 100. Aspiration tube 108 can fit coaxially within infusion sleeve 102 and both can couple to handpiece 113 (see FIG. 1) at their respective proximal ends. Handpiece 113 can provide communication paths from ophthalmic tubing 115 (see FIG. 1) to and from, respectively, infusion sleeve 102 and aspiration tube 108. Thus, infusion fluid can be directed distally through infusion sleeve 102 and out through infusion port 106 in a direction perpendicular to longitudinal axis 122. Aspiration port 110 of infusion/aspiration tip 104 can draw material from its environment (for instance, lens 18 of FIG. 1) for return to, for example, an infusion/aspiration machine via aspiration tube 108. The direction from which aspiration port 110 can draw material can be perpendicular to the direction in which infusion port 106 directs fluid.

Figure 3:
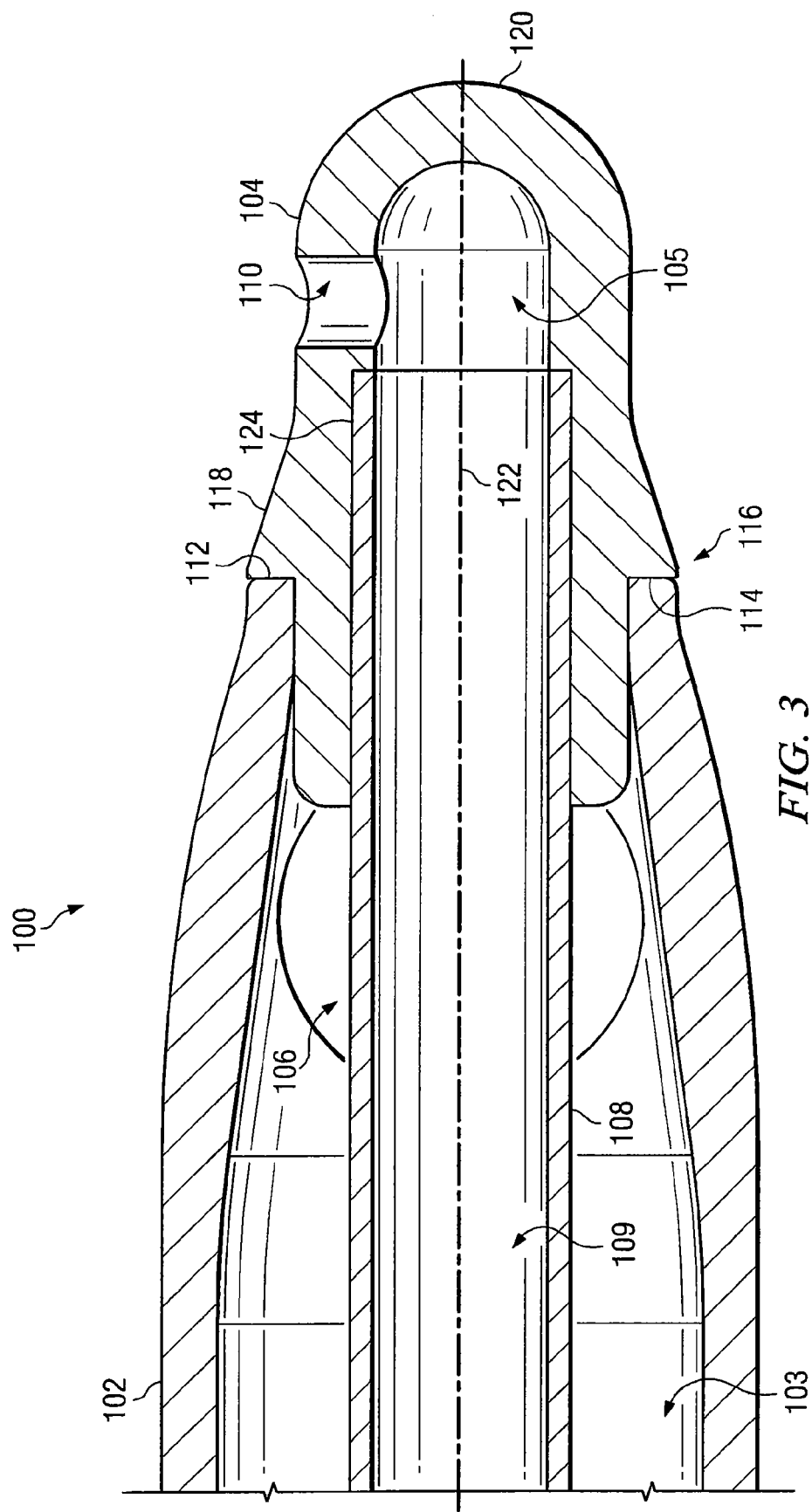
FIG. 3 is a cross sectional view of one embodiment of an ophthalmic surgical instrument.

FIG. 3 illustrates a cross sectional view of one embodiment of instrument 100. Furthermore, FIG. 3 illustrates infusion sleeve 102; infusion channel 103; irrigation/aspiration tip 104; aspiration channel 105; infusion port 106; aspiration tube 108; aspiration channel 109; aspiration aperture 110; distal end 112 of infusion sleeve 102; flange 114; proximal end 116 of infusion/aspiration tip 104; tapered portion 118; distal end 120 of infusion/aspiration tip 104; longitudinal axis 122; and distal end 124 of aspiration tube 108. More particularly, FIG. 3 illustrates infusion/aspiration tip 104 being coupled to and conforming to distal end 124 of aspiration tube 108. In some embodiments, infusion/aspiration tip 104 can be overmolded onto aspiration tube 108. Aspiration channel 105 of infusion/aspiration tip 104 can align with and correspond to aspiration channel 109 of aspiration tube 108. In some embodiments, aspiration channel 105 of infusion/aspiration tip 104 can extend distally beyond aspiration port 110. Aspiration channel 105 of infusion/aspiration tip 104 can communicate with aspiration port 110 thereby allowing instrument 100 to aspirate material generally adjacent to infusion/aspiration tip 104 through aspiration port 110, aspiration channel 105 of infusion/aspiration tip 104, and aspiration channel 109 of aspiration tube 108 (and then through ophthalmic tubing 115 for disposal). From aspiration channel 109 of aspiration tube 108, aspirated material can be returned to an infusion/aspiration machine (or other system for disposal) via ophthalmic tubing 115 (see FIG. 1).

Flange 114 of infusion/aspiration tip 104 can abut distal end 112 of infusion sleeve 102 and can seal infusion channel 103 against leakage from distal end 112 of infusion sleeve 102. Infusion/aspiration tip 104 can extend into infusion channel 103 some distance thereby also sealing against the internal walls of infusion sleeve 102. Furthermore, infusion/aspiration tip 104 can extend into infusion sleeve 102 to a point adjacent to a portion of infusion port 106 thereby blocking flow through infusion channel 103 and directing infusion fluid out through infusion port 106. In some embodiments, the interior surface of infusion sleeve 102 can taper away from infusion/aspiration tip 104 in the vicinity of infusion port 106, thereby allowing flow through infusion port 106 passed infusion/aspiration tip 104. In some embodiments, infusion/aspiration tip 104 can be retained in infusion sleeve 102 by friction between infusion/aspiration tip 104 and the internal walls of infusion sleeve 102 despite pressure within infusion channel 103. For instance, infusion/aspiration tip 104 and infusion sleeve 102 can be shaped and dimensioned to create an interference fit when infusion/aspiration tip 104 is inserted into infusion sleeve 102. Alternatively, some clearance can exist between infusion/aspiration tip 104 and infusion sleeve 102. In some embodiments, infusion/aspiration tip 104 can be indirectly coupled to handpiece 113 (see FIG. 1) by aspiration tube 108, thereby allowing it to remain in infusion sleeve 102 despite pressure therein. The indirect coupling of infusion/aspiration tip 104 and handpiece 113 can hold infusion/aspiration tip 104 against distal end 112 of infusion sleeve 102 thereby creating a seal between these two components 104 and 102. Thus, infusion/aspiration tip 104 can prevent leakage of infusion fluid from infusion sleeve 102 in a direction along longitudinal axis 122.

FIG. 3 also illustrates infusion/aspiration tip 104 including tapered portion 118. Tapered portion 118 can have a diameter at proximal end 116 of infusion/aspiration tip 104 which is about the same as the diameter of distal end 112 of infusion sleeve 102. Thus, the profile of infusion/aspiration tip 104 can correspond to the profile of infusion sleeve 102. Tapered portion 118 can taper to another, smaller diameter some distance from proximal end 116 of infusion/aspiration tip 104. Thus, the interface between infusion/aspiration tip 104 and infusion sleeve 102, can be smooth and offer little or no resistance to inserting instrument 100 into eye 10 (see FIG. 1). From the distal end of tapered portion 118, the surface of infusion/aspiration tip 104 can be parallel to longitudinal axis 122 from approximately tapered portion 118 to approximately the distal edge of aspiration port 110.

Infusion/aspiration tip 104 can be formed from various plastics, elastomers, etc. while infusion sleeve 102 and aspiration tube 108 can be formed from stainless steel, titanium, or any other biocompatible material. In some embodiments, infusion/aspiration tip 104 is made from a plastic material such as Makrolon® 2558 (which is available from Bayer MaterialScience L.L.C. of Pittsburgh, Pa.). Thus, infusion/aspiration tip 104 can have a smooth surface free of sharp edges, micro burrs, etc. Accordingly, infusion/aspiration tips 104 of various embodiments can avoid tearing capsular bag 19, thereby speeding patient recovery and reducing patient discomfort associated with certain ophthalmic surgical procedures.

Moreover, instrument 100 can be quickly assembled by surgical personnel. Instrument 100 can be assembled by sliding aspiration tube 108 (with infusion/aspiration tip 104 overmolded thereon) into infusion sleeve 102. As infusion/aspiration tip 104 approaches distal end 112 of infusion sleeve 102, surgical personnel can align infusion/aspiration tip 104 and distal end 112 of infusion sleeve 102. Surgical personnel can push infusion/aspiration tip 104 into infusion channel 103 thereby sealing distal end 112 of infusion sleeve 102. Surgical personnel can, when desired, connect infusion sleeve 102 and aspiration tube 108 to handpiece 113, ophthalmic tubing 115, etc. (see FIG. 1).

Surgical personnel can navigate instrument 100 to the vicinity of eye 10 and begin to insert distal end 120 of infusion/aspiration tip 104 into an incision therein. As infusion/aspiration tip 104 enters eye 10, smooth surfaces of infusion/aspiration tip 104 can distract tissues it encounters without tearing capsular bag 19 or otherwise traumatizing eye 10. As surgical personnel advance instrument 100 into eye 10, tapered portion 118 can also distract tissues without tearing capsular bag 19 or otherwise traumatizing eye 10. Surgical personnel can therefore manipulate instrument 100 to extract cataracts and other tissues as may be desired. When desired, surgical personnel can withdraw instrument 100 from eye 10.

Surgical personnel can disassemble instrument 100 and dispose of infusion/aspiration tip 104 and aspiration tube 108. Infusion/aspiration tip 104 and aspiration tube 108 can be relatively inexpensive to manufacture thereby allowing such single uses of infusion/aspiration tip 104 and aspiration tube 108. Thus, embodiments can alleviate surgical personnel from the need to clean and sterilize infusion/aspiration tip 104 and aspiration tube 108 following various surgical procedures. Moreover, because infusion/aspiration tip 104 and aspiration tube 108 can be pre-sterilized, the need for surgical personnel to clean and sterilize infusion/aspiration tip 104 and aspiration tube 108 (including any crevice that might exist between infusion sleeve 102 and infusion/aspiration tip 104) prior to certain ophthalmic surgical procedures can be alleviated by various embodiments.

Figure 4:
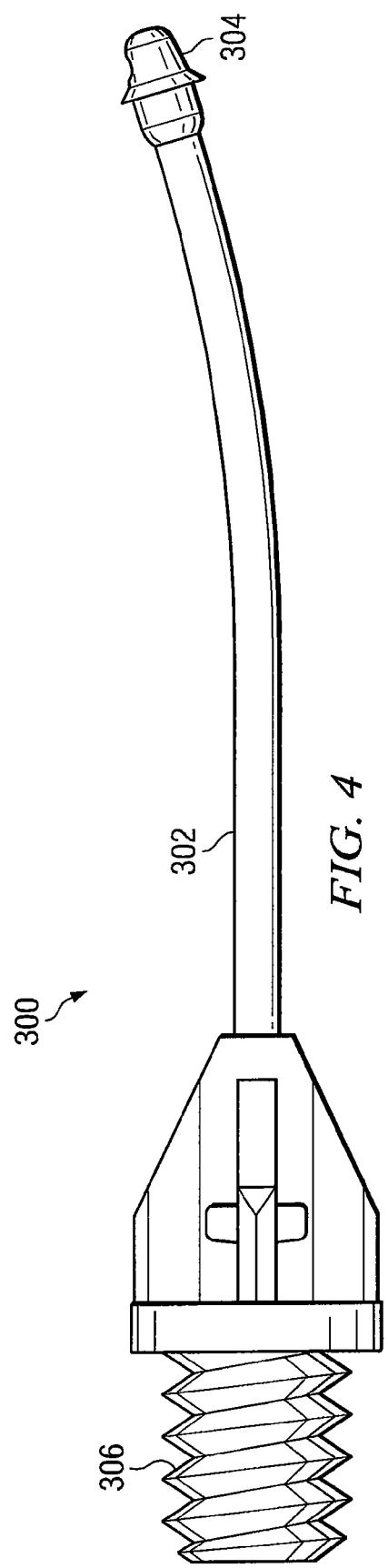
FIG. 4 is a diagrammatic representation of an embodiment of a curved ophthalmic instrument.
Figure 5:
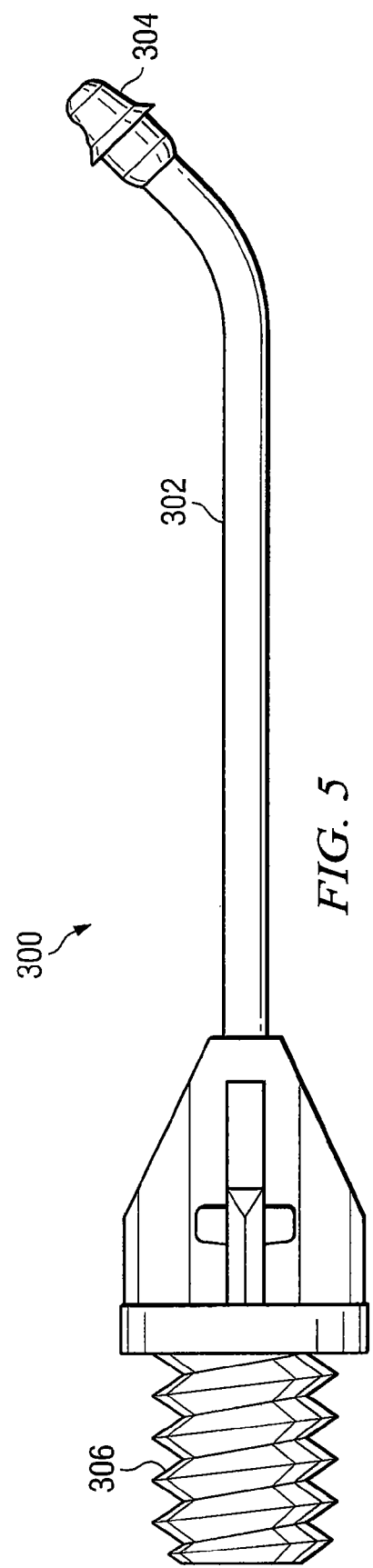
FIG. 5 is a diagrammatic representation of an embodiment of a bent ophthalmic instrument.

In the previous embodiments, the surgical instrument has a generally straight profile. In FIG. 4, one the other hand, surgical instrument 300 can have a curved profile. In FIG. 4, instrument 300 can include aspiration sleeve 302, infusion/aspiration tip 304, and an attachment portion 306 for attachment to a hand piece. The radius of curvature of aspiration tube 302 can be selected to be extend the entire length of aspiration tube 302 or a portion of the length. One or more sections of aspiration tube 302 can remain straight when the tube is curved. As shown in FIG. 5, the curved section may be relatively small and have a small radius, while the remainder of aspiration tube 302 remains straight to give the instrument a bent appearance. For example a straight portion can run from attachment portion 306 to the curved section and another straight portion can run from the curved section to infusion/aspiration tip 304. In other embodiments, a bent profile can be achieved using a non-curved interface between straight sections.

While the disclosure has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

What is claimed is:

1. An ophthalmic surgical instrument comprising:
    an infusion sleeve comprising an elongated body defining an infusion channel and having a proximal end, a distal end, and a longitudinal axis along the length of the elongated body;
    an aspiration tube defining an aspiration channel, having a proximal end and a distal end, and being positioned in the infusion channel; and an infusion/aspiration tip formed of plastic coupled to and conforming to the distal end of the aspiration tube, wherein the infusion/aspiration tip is overmolded onto the aspiration tube, wherein the infusion/aspiration tip further comprises a proximal end and a flange formed along an outer surface of the infusion/aspiration tip, wherein the proximal end of the infusion/aspiration tip is accepted into the infusion channel at a distal end of the infusion sleeve, and wherein the distal end of the infusion sleeve abuts the flange of the infusion/aspiration tip.

2. The instrument of claim 1 wherein a gap exists between the distal end of the infusion sleeve and the distal end of the aspiration tube and wherein the infusion/aspiration tip seals the gap.

3. The instrument of claim 1 wherein the infusion sleeve defines an infusion port oriented to direct infusion fluid from the infusion channel in a first direction which is perpendicular to the longitudinal axis.

4. The instrument of claim 3 wherein the infusion/aspiration tip defines an aspiration port oriented to draw material from the environment in a second direction which is perpendicular to the longitudinal axis and wherein the first and the second directions are perpendicular to each other.

5. The instrument of claim 4 wherein the infusion/aspiration tip defines an extension of the aspiration channel which extends distally beyond the aspiration port.

6. The instrument of claim 3 wherein the infusion/aspiration tip extends in a direction along the longitudinal axis to a point adjacent to the infusion port.

7. The instrument of claim 1, wherein the infusion/aspiration tip defines a tapered portion.

8. An ophthalmic surgical instrument comprising:
an infusion sleeve comprising an elongated body defining an infusion channel and having a proximal end, a tapered distal end, and a longitudinal axis along the length of the elongated body, the infusion sleeve defining an infusion port oriented to direct infusion fluid from the infusion channel in a first direction which is perpendicular to the longitudinal axis;
an aspiration tube defining an aspiration channel, having a proximal end and a distal end, and being positioned in the infusion channel; and
an infusion/aspiration tip comprising a distal tip, a tapered portion, and an aspiration port disposed between the distal tip and the tapered portion, the tapered portion disposed adjacent to the tapered distal end of the infusion sleeve to define a tapered exterior surface.

9. The ophthalmic surgical instrument of claim 8, wherein the distal end of the aspiration tube extends longitudinally beyond the distal end of the infusion sleeve.

10. The ophthalmic surgical instrument of claim 8, wherein the infusion/aspiration tip comprises a proximal end and wherein the proximal end of the infusion/aspiration tip terminates at a point adjacent to a portion of the infusion port.

11. The instrument of claim 8, wherein the infusion/aspiration tip is coupled to and conforming to the distal end of the aspiration tube, wherein a gap exists between the distal end of the infusion sleeve and the distal end of the aspiration tube, wherein the infusion/aspiration tip seals the gap and wherein the infusion/aspiration tip defines an aspiration port oriented to draw material from the environment in a second direction which is perpendicular to the longitudinal axis and wherein the first and the second directions are perpendicular to each other, wherein the infusion/aspiration tip defines an extension of the aspiration channel which extends distally beyond the aspiration port, and wherein the infusion/aspiration tip extends in a direction along the longitudinal axis to a point adjacent to the infusion port.

12. A single use, disposable component to be coupled to an ophthalmic surgical instrument wherein the instrument includes an infusion sleeve comprising an elongated body defining an infusion channel and having a proximal end, a tapered distal end, and a longitudinal axis along the length of the elongated body, the component comprising:
an aspiration tube defining an aspiration channel, having a proximal end and a distal end, and to be positioned in the infusion channel; and
an infusion/aspiration tip formed of plastic coupled to and conforming to the distal end of the aspiration tube, the infusion/aspiration tip comprising:
a proximal end;
a distal tip;
an aspiration port; and
a tapered portion disposed between the aspiration port and the proximal end, the proximal end received into the tapered distal end of the infusion sleeve such that the tapered distal end of the infusion sleeve and the tapered portion of the infusion/aspiration tip define a tapered exterior surface.

13. Original) The disposable component of claim 12 wherein when the disposable component is coupled to the instrument a gap exists between the distal end of the infusion sleeve and the distal end of the aspiration tube and wherein the infusion/aspiration tip seals the gap.

14. The disposable component of claim 12 wherein the infusion sleeve defines an infusion port oriented to direct infusion fluid from the infusion channel in a first direction which is perpendicular to the longitudinal axis.

15. The instrument of claim 14 wherein the infusion/aspiration tip defines an aspiration port oriented to draw material from the environment in a second direction which is perpendicular to the longitudinal axis and wherein the first and the second directions are perpendicular to each other when the disposable component is coupled to the instrument.

16. The disposable component of claim 15 and wherein the infusion/aspiration tip defines an extension of the aspiration channel which extends distally beyond the aspiration port.

17. The disposable component of claim 14 wherein the infusion/aspiration tip extends in a direction along the longitudinal axis to a point adjacent to the infusion port when the disposable component is coupled to the instrument.

18. The ophthalmic surgical instrument of claim 1, wherein the distal end of the aspiration tube extends longitudinally beyond the distal end of the infusion sleeve.

19. The ophthalmic surgical instrument of claim 1, wherein a proximal end of the infusion/aspiration tip comprises a bore and wherein the distal end of the aspiration tube is received into the bore.

20. The ophthalmic surgical instrument of claim 1, wherein the infusion sleeve further comprises an infusion port, wherein the infusion/aspiration tip comprises a proximal end, and wherein the proximal end of the infusion/aspiration tip terminates at a point adjacent to a portion of the infusion port.

21. The disposable component of claim 12, wherein the distal end of the aspiration tube extends longitudinally beyond the distal end of the infusion sleeve.

22. The disposable component of claim 12, wherein a proximal end of the infusion/aspiration tip comprises a bore and wherein the distal end of the aspiration tube is received into the bore.

23. The disposable component of claim 12, wherein the infusion/aspiration tip further comprises a proximal end and a flange formed along an outer surface of the infusion/aspiration tip, wherein the proximal end of the infusion/aspiration tip is accepted into the infusion channel at a distal end of the infusion sleeve, and wherein the distal end of the infusion sleeve abuts the flange of the infusion/aspiration tip.

24. The disposable component of claim 12, wherein the infusion sleeve further comprises an infusion port, wherein the infusion/aspiration tip comprises a proximal end, and wherein the proximal end of the infusion/aspiration tip terminates at a point adjacent to a portion of the infusion port.

25. The disposable component of claim 12, wherein the infusion/aspiration tip further comprises a flange and wherein the tapered distal end of the infusion sleeve abuts the flange.

26. An ophthalmic surgical instrument comprising:
an infusion sleeve comprising:
- an elongated body defining an infusion channel;
- a proximal end;
- a tapered distal end; and
- a longitudinal axis along the length of the elongated body;

an aspiration tube defining a first aspiration channel, having a proximal end and a distal end, and being positioned in the infusion channel; and an infusion/aspiration tip coupled to the tapered distal end of the infusion sleeve, the infusion/aspiration tip comprising:
- a second aspiration channel in fluid communication with the first aspiration channel of the aspiration tube;
- an aspiration port in communication with the second aspiration channel; and
- a tapered portion formed on an exterior surface at a location proximal to the aspiration port, the tapered portion disposed adjacent to the tapered distal end of the infusion sleeve to define a tapered exterior surface, the distal end of the aspiration tube received into the second aspiration channel of the infusion/aspiration tip.

* * * * *